United States Patent [19]

Sander et al.

[11] Patent Number: 4,744,792
[45] Date of Patent: May 17, 1988

[54] MIDDLE EAR VENTILATING TUBE

[75] Inventors: Thomas W. Sander, Southaven, Miss.; Karen Krygier, Memphis, Tenn.

[73] Assignee: Richards Medical Company, Memphis, Tenn.

[21] Appl. No.: 693,155

[22] Filed: Jan. 22, 1985

[51] Int. Cl.[4] .............................................. A61F 2/18
[52] U.S. Cl. ................................................ 623/10
[58] Field of Search ............... 128/1 R, 329 R, 151; 604/174, 264, 266, 328; 3/1; 623/10, 11, 12, 16, 18

[56] References Cited

U.S. PATENT DOCUMENTS

| 3,425,418 | 2/1969 | Chvapil et al. | 623/1 |
| 3,807,409 | 4/1974 | Paparella | 3/1 |
| 3,914,802 | 10/1975 | Reick | 623/1 |
| 3,975,350 | 8/1976 | Hudgin et al. | 3/1 |
| 4,052,754 | 10/1977 | Homsy | 623/10 |
| 4,094,303 | 6/1978 | Johnston | 3/1 D |
| 4,168,697 | 9/1979 | Cantekin | 3/1 D |
| 4,286,341 | 9/1981 | Greer et al. | 623/1 |
| 4,527,293 | 7/1985 | Eckstein et al. | 604/266 |

Primary Examiner—Richard J. Apley
Assistant Examiner—David J. Isabella
Attorney, Agent, or Firm—Pravel, Gambrell, Hewitt, Kimball & Krieger

[57] ABSTRACT

A ventilation tube is provided for permitting gaseous communication between the middle ear and the outer ear canal of a recipient. The tube is formed of a material that resists extrusion from the tympanic membrane such as titanium or a titanium alloy or others, and includes an outer end portion which is adapted to communicate with the outer ear canal and an inner ear portion adapted to communicate with the middle ear. A pair of spaced apart flanges are mounted respectively on the outer end portion and the inner end portion of the tube. A coating or insert formed of a material that resists tissue adherence such as a fluoroplastic polymer (e.g., Teflon) or others lines at least the portion of the opening in the tube adjacent to the middle ear and the flange on the middle ear side of the tympanic membrane.

13 Claims, 2 Drawing Sheets

MIDDLE EAR VENTILATING TUBE

FIELD OF THE INVENTION

The present invention relates to prosthetic devices such as ventilation or drain tubes that are surgically inserted in the tympanic membrane of the ear. Such tubes are useful for equalizing pressure between the middle and outer ear canals and draining fluid build-up associated with otitis media from the middle ear.

BACKGROUND OF THE INVENTION

By way of background, the typical remedy for middle ear effusion is a myringotomy, which is a surgical procedure that involves cutting a slit or opening in the tympanic membrane of a patient in order to alleviate a buildup or reduction of pressure in the middle ear cavity and to drain accumulated fluids.

A variety of ear ventilation tubes for insertion into such an opening or slit in the tympanic membrane have been developed. For example, a chronology of middle ear ventilation tubes developed over the years is provided in the article "Middle Ear Ventilation Tubes", by James J. Pappas, M.D. in "The Laryngoscope", 1974.

Frequently the condition of buildup or reduction of pressure in the middle ear cavity, which a ventilation tube is intended to alleviate, requires that the tube remain in place for significant period of time. As discussed in the Pappas article, ventilation tubes have had a variety of configurations and it is also known that such tubes have been made of various materials.

One problem associated with ventilation tubes is clogging over a period of time, which may be caused by epithelial tissue migration, occlusion by middle ear effusions or possibly cerumen (wax) build-up. Tubes made of a polymer such as a fluorocarbon have experienced a relatively low incidence of clogging. However, such tubes will typically extrude from the tympanic membrane within a relatively short time period of, for example, six to nine months. The use of polymer tube is discussed in an article by Karlan et al entitled "Myringotomy Tube Materials: Bacterial Adhesion and Infection" published in the Nov.-Dec. 1980 issue of *Otolaryngol Head Neck Surgery*.

Vent tubes have also been formed of silicon rubber or other biocompatible materials. One such tube, which includes a fluorocarbon membrane over the outer opening to prevent the passage of liquid but allows air flow, is taught in U.S. Pat. No. 3,916,873. Tissue is prevented from growing over the vent opening by placing an anti-coagulate coating over the membrane. However, even though the membrane is porous it is still subject to clogging easily and does not provide the degree of ventilation of an open tube and does not permit fluid to drain outwardly.

Although vent tubes formed of titanium or titanium alloys have been known to resist extrusion, they have also exhibited the problem of clogging. This significantly reduces the effectiveness of such tubes because many patients require long term ventilation.

SUMMARY OF THE INVENTION

According to the present invention, a ventilation tube for the middle ear has been developed that resists extrusion and, at the same time, maintains an unobstructed ventilation opening. The tube is formed as a composite of a material that resists extrusion combined with a material that resists tissue adherence.

The subject tube includes an outer portion formed of an extrusion resistant material such as titanium or titanium alloy, calcium phosphate based ceramics such as tricalcium phosphate, hydroxylaptite or bioglass, aluminum oxide ceramics, and vitreous or pyrolytic carbon. The tube has an outer end adapted to communicate with the outer ear canal and an inner end adapted to communicate with the middle ear. A pair of spaced apart flanges are formed on the outer and inner end portions of the tube to hold the tube in place in an opening surgically formed in the tympanic membrane.

The tube has an open-ended bore or lumen for providing an opening in the tympanic membrane so that pressure is equalized between the recipient's middle ear and the outer ear canal. A liner or coating formed of materials such as a fluoroplastic, polyethylene, polypyropylene or hydrogel, which resist tissue adhesion, lines or coats the portion of the bore adjacent to the middle ear and at least the end of the tube on the middle ear side of the tympanic membrane, and possibly the entire inner and outer surface area that does not engage the tympanic membrane, depending on tube shape and manufacturing techniques. This liner or coating resists tissue adhesion or adherence and prevents the tube opening from clogging.

BRIEF DESCRIPTION OF THE DRAWINGS

A better understanding of the invention can be had when the detailed description of a preferred embodiment set forth below is considered in conjunction with the drawings, in which.

DETAILED DESCRIPTION OF PREFERRED EMBODIMENTS

Figure 1:
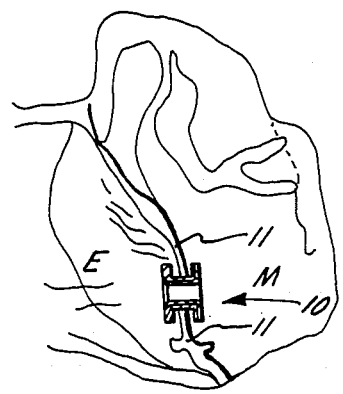
FIG. 1 is a cross-sectional view of a middle ear showing a preferred embodiment of a myringotomy tube of the present invention inserted in the tympanic membrane.
Figure 3:
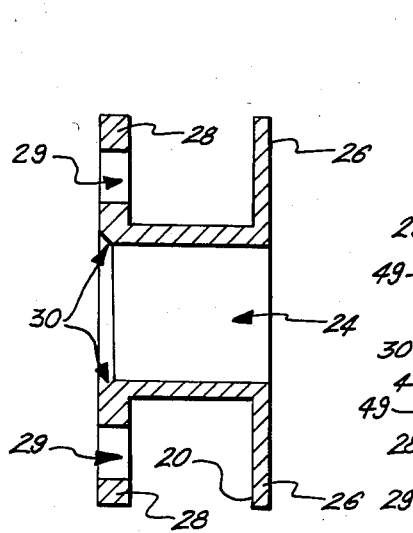
FIG. 3 is a cross-sectional view of the main body portion of the tube of FIG. 1, formed of a material that resists extrusion.

Referring to the drawings, FIG. 1 shows one preferred embodiment of the ventilation tube of the present invention, which is designated generally by reference numeral 10. The tube 10 is surgically inserted in a tympanic membrane 11 of a recipient's ear between middle ear M and outer ear E. This surgical procedure has become relatively routine and does not need to be discussed further.

One embodiment of the subject ventilation tube is shown in detail in FIGS. 2–5, where the tube 10 includes a main tube body 20 that has a central tubular portion 22 through which is formed an open-ended bore 24. A pair of flanges 26, 28 are formed on the ends of the central tubular portion 22 such that the vent tube resembles a bobbin.

The flange 28 may or may not have a plurality of radially-spaced openings 29 for providing sites for forceps to grasp the tube to facilitate insertion. The openings also help to reduce the weight of the tube. The bore 24 includes an end portion 30 on the end of the tube that will be positioned on the side of the tympanic membrane 11 adjacent to the outer ear canal E (see FIG. 1), which has an annular beveled or flared end 30 that cooperates with an insert 40 as hereinafter described.

The tube 20 as described above is formed as an integral unit of a material which resists epithelial extrusion from the tympanic membrane 11. Suitable materials for these purposes include titanium or a titanium alloy, calcium phosphate, ceramics such as hydroxylapatite, tricalcium phosphate or the bioglasses, aluminum oxide ceramics, and vitreous or pyrolytic carbon. These materials have been shown in the past to be conducive to tissue adhering to the outer surface of a vent tube and holding it in place in a tympanic membrane and resisting extrusion. Such a tube is useful for patients who require a vent tube to remain in the tympanic membrane for long periods of time. However, because of the properties of materials to which tissue easily adheres, tissue may have a tendency to grow over the ends of the tube and contribute to clogging of the opening.

Figure 2:
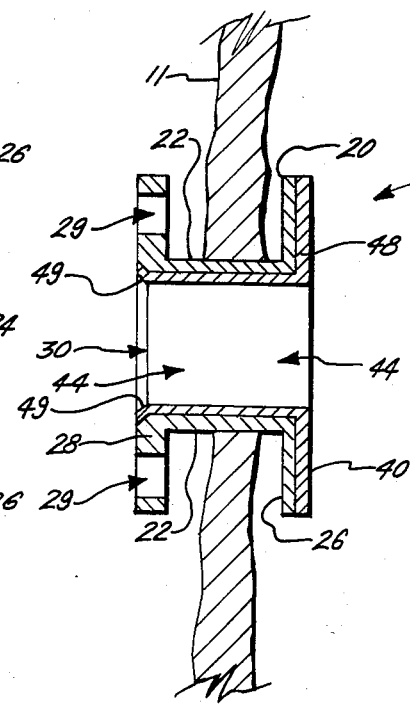
FIG. 2 is an enlarged cross-sectional view of the tube shown in FIG. 1.
Figure 4:
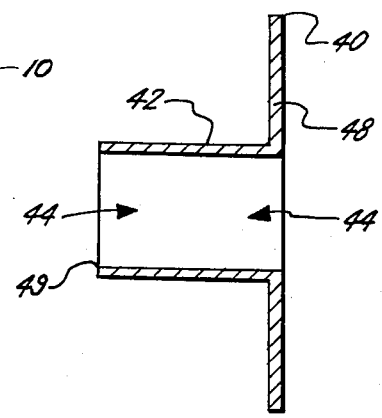
FIG. 4 is a cross-sectional view of the insert portion of the tube of FIG. 1, formed of a material that resists tissue adherence.
Figure 5:
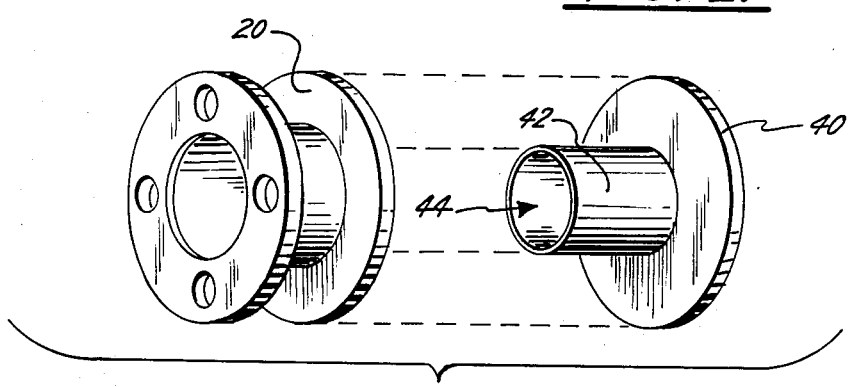
FIG. 5 is an exploded perspective view of the myringotomy tube formed of the sections shown in FIGS. 3 and 4.

One embodiment of a tube designed to solve this problem is shown best in FIGS. 2, 4 and 5 where a liner is provided for insertion into the bore 24. The linear 40 includes a cylindrical tube portion 42 with an outer diameter that is virtually the same as that of the bore 24 so that the tube 42 will snugly fit in the bore 24. The liner 40 also includes an internal bore 44 for providing open communication between the middle ear canal M and outer ear E.

The liner 40 also includes a flange portion 48 that fits over the flange 26 of the tube 20. As shown in FIG. 5, the liner 40 is inserted into the tube 20 on the side of the flange 26 and provides a liner for the surface that defines the bore 24 and the outer end of the flange 26. After the liner 40 has been inserted to the position shown in FIG. 2, its outer end 49 is press fitted into engagement with the flared end portion 30 of the tube 20 for holding the liner 40 in place and preventing it from being easily removed from the tube 20.

The liner is formed of a material that resists tissue adhesion such as, for example, a fluorocarbon polymer known as Teflon (a registered trademark of E.I. duPont), polyethylene, polypropylene or hydrogels. It is believed that by providing at least the portion of the bore adjacent to the inner end and the inner end of a vent tube of such a material, tissue will not grow over and clog the opening, as it does for materials that resist extrusion, as described above. This design has the effect of preventing the opening of the tube 20 from being clogged after it has been implanted for relatively long periods of time.

Figure 6:
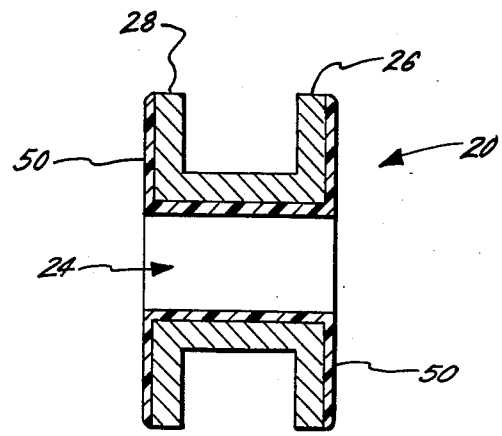
FIG. 6 is a cross-sectional view of an embodiment of the invention with a coating of adhesion resistant material instead of the liner of FIGS. 2, 4 and 5.
Figures 7, 8:
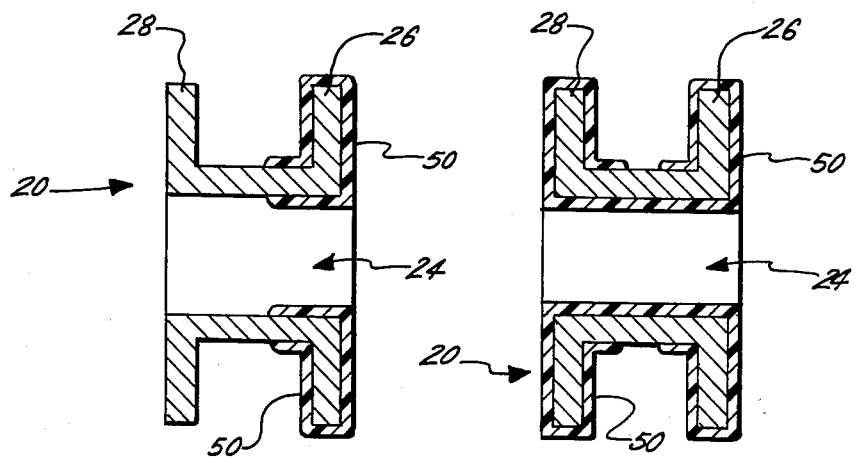
FIGS. 7 and 8 are cross-sectional views of other embodiments of the invention where a coating of adhesion resistant material is formed on various portions of the exposed surfaces of the tube.

In another embodiment of the invention as shown in FIG. 6, the tube 20 includes a coating 50 of adhesive resistant material on the outer surfaces of the flanges 26, 28 and surface that defines the bore 24 or, as illustrated in FIG. 7, the coating 50 is applied only to the exposed surfaces of the tube 20 that project into the middle ear M. This coating 50 can be applied by spraying, dipping or the like, with surfaces not to be coated appropriately masked. In another embodiment, as shown in FIG. 8, the coating 50 can extend to all surfaces of the tube 20 that are not in contact with the tympanic membrane 11. An important feature of the invention is to form the portion of the tube that engages the tympanic membrane of an extrusion resistant material and the exposed surfaces of the tube such as at least the portion of the bore and end of the tube adjacent to the middle ear of adherence resistant material.

In this way, a vent tube is formed of materials with different characteristics that solve the problems discussed above. A vent tube formed with an extrusion resistant surface for engaging the tympanic membrane and adhesion resistant surface for at least the portion of the exposed surfaces of the tube adjacent to the middle ear, utilizes the advantages of both materials and eliminates their individual disadvantages. In this way, a long-term vent tube is provided which will remain open while it remains in service.

The foregoing disclosure and description of the invention are illustrative and explanatory thereof, and various changes in the size, shape and materials, as well as in the details of the illustrated construction may be made without departing from the spirit of the invention.

We claim:

1. A composite ventilation tube adapted to be inserted in and engage the tympanic membrane portion of an ear, between the middle ear and outer ear canal, comprising:
   (a) a main tubular body with an outer surface and an inner surface forming a bore with openings at both ends for venting fluids from the middle ear the outer ear canal;
   (b) at least the central portion of the outer surface that engages the tympanic membrane during use being formed of an extrusion resistant material so that the adjacent tissue growth about the outer surface of the main tubular body is permitted without substantial tissue ingrowth to resist but not prevent extrusion from the tympanic membrane;
   (c) at least the portion of said inner surface adjacent the middle ear during use having a tissue adhesion resistant lining to prevent the tube from clogging; and
   (d) means for holding the tubular body in a position upon the tympanic membrane projecting from the tubular body.

2. The ventilation tube of claim 1, wherein said lining material is from a group consisting of: titanium, titanium alloy, hydroxylapatite, tricalcium phosphate, aluminum oxide, bioglass vitreous carbon and pyrolytic carbon.

3. The ventilation tube of claim 1, wherein said lining material is from a group consisting of: fluoroplastics, polyethylenes, polypropylenes and hydrogels.

4. The ventilation tube of claim 1, wherein the lining material is formed of a titanium alloy.

5. The ventilation tube claim 1, wherein the lining material is formed of fluoroplastic.

6. The ventilation tube of claim 1, wherein the main tube body includes flange means formed on both ends of the tube body for holding said tube body in the tympanic membrane.

7. The ventilation tube of claim 6, wherein the tube is formed as a composite of a main tube body formed of extrusion resistant material, and a liner portion formed of said adherence resistant material for lining the opening and outer end of the flange adapted to be positioned on the side of the tympanic membrane adjacent to the middle ear.

8. The ventilation tube of claim 7, wherein said opening includes a flared portion on the end of the tube adapted to be positioned on the side of the tympanic membrane adjacent to the outer ear, the liner including a flared end adapted to cooperate with the flared portion of the opening for holding the liner in the tube.

9. The ventilation tube of claim 1, wherein said tube is formed as a composite of a main tube body formed of extrusion resistant material with flanges on each end, and a coating of said adherence resistant material.

10. The ventilation tube of claim 9, wherein the coating of said adherence resistant material extends along the entire inner surface.

11. The ventilation tube of claim 9, wherein said coating is applied to the outer ends of both flanges.

12. The ventilation tube of claim 9, wherein said coating is applied to the portion of the outer surface of the tube body adapted to be located on the middle side of the tympanic membrane.

13. The ventilation tube of claim 9, wherein said coating is applied to the entire exposed surface of the tube not adapted to engage the tympanic membrane.

* * * * *